United States Patent [19]

Fife et al.

[11] Patent Number: 5,705,581
[45] Date of Patent: Jan. 6, 1998

[54] FLUORIDE ION RELEASING DENTAL MATERIALS

[75] Inventors: Wilmer K. Fife, Indianapolis, Ind.; Martel Zeldin, Staten Island; Slawomir Rubinsztajn, Schenectady, both of N.Y.

[73] Assignee: Indiana University Foundation, Bloomington, Ind.

[21] Appl. No.: 474,162

[22] Filed: Jun. 7, 1995

Related U.S. Application Data

[62] Division of Ser. No. 378,657, Jan. 26, 1995, Pat. No. 5,639,840.

[51] Int. Cl.⁶ .......................... C08F 20/60; A61K 6/083
[52] U.S. Cl. .......................... 526/248; 523/115; 523/116; 523/118; 523/310; 523/482; 524/555
[58] Field of Search .......................... 526/248; 523/115, 523/116, 310, 118, 482; 524/555

[56] References Cited

U.S. PATENT DOCUMENTS

| | | | |
|---|---|---|---|
| 3,962,332 | 6/1976 | Trapasso et al. | 564/204 |
| 4,515,910 | 5/1985 | Rawls et al. | 523/115 |
| 4,572,920 | 2/1986 | Rawls et al. | 523/115 |
| 4,621,120 | 11/1986 | Hollister | 524/555 |
| 4,871,786 | 10/1989 | Aasen et al. | 523/113 |
| 4,981,936 | 1/1991 | Good, Jr. et al. | 526/287 |

*Primary Examiner*—Andrew E. C. Merriam
*Attorney, Agent, or Firm*—Woodard, Emhardt, Naughton Moriarty & McNett

[57] ABSTRACT

Described are novel fluoride ion-releasing acrylic or methacrylic acid-based monomers, fluoride ion-releasing dental resin materials prepared from the monomers, and processes for preparing the monomers and dental resin materials. The monomers of the invention are prepared in good yield from readily available starting materials. Dental resin materials of the invention exhibit excellent sustained fluoride ion release.

16 Claims, No Drawings

FLUORIDE ION RELEASING DENTAL MATERIALS

This application is a division of application Ser. No. 08/378,657, filed Jan. 26, 1995, now U.S. Pat. No. 5,639,840.

BACKGROUND

This invention pertains to novel fluoride ion-releasing polymerizable acrylic and methacrylic acid derivatives, and to their preparation and use in fluoride-ion releasing resins which have use in dental applications.

The fluoride ion has long been recognized as an effective agent for reducing carious attack and demineralization of tooth structure. For this reason, there has been interest in incorporating fluoride ion in dental materials.

The most widely used fluoride-containing substances added to dental resin materials are sodium fluoride, stannous fluoride, and certain ammonia fluorides. Attempts have been made to incorporate such inorganic fluoride salts into cavity liners, sealants, coatings, orthodontic bracket adhesives and amalgams. However, a primary problem with incorporation of inorganic fluoride-containing salts into dental resins is an inherent incompatibility caused by a large difference in polarity between the ionic fluoride salt and the low-polarity dental resin, the latter being an organic material. Incompatibility usually causes phase separation with the resin, loss of mechanical integrity of the resin and rapid fluoride ion release within the first few hours of use. Incorporation of low molecular weight organic fluoride species has a plasticizing effect which leads to similar undesirable results.

Kadoma et al., *Macromol. Chem.* 1981, 182, 273 and *Macromolecules* 1982, 15, 1119, synthesized a fluoride ion releasing methacryloyl fluoride-methylmethacrylate copolymer, in which the fluorine is covalently bonded to a carbonyl group. This resulted in the slow release of the fluorine as fluoride ion by hydrolysis of the acid fluoride in aqueous solution. It has been shown that this copolymer can be incorporated into experimental sealants and will release fluoride slowly. Tanaka et al., *J. Dent. Res.* 1987, 66, 1591; and Nishida et al., JP 62-012,706 (1987).

Rawls et al., U.S. Pat. Nos. 4,515,910 (1985) and 4,572,920 (1986), incorporated fluoride ion as a mobile charge into an acrylic anion exchange resin. These studies demonstrated that t-butylaminoethyl methacrylate hydrogen fluoride can be copolymerized readily with other acrylic monomers and can serve as a source of fluoride ion in the final resin. These resins were tested as fissure sealants, orthodontic cements and resin materials.

In light of this background there remains a need for further compounds which can be used in the preparation of fluoride ion-releasing dental materials. Desirably, the compounds would be prepared from readily available starting materials, and provide dental materials with acceptable levels of sustained fluoride ion release while exhibiting acceptable hardness and resistance to deterioration. The present invention addresses these needs.

SUMMARY OF THE INVENTION

The present invention provides novel polymerizable, fluoride ion-releasing monomers, methods for their preparation and use, and dental resin compositions prepared from the novel monomers. Accordingly, one preferred embodiment of the invention provides fluoride-releasing acrylamide or methacrylamide monomers bearing ion-exchange or chelation sites carrying fluoride ion or a fluoride-containing anion, which exhibit superior stability over related esters in aqueous and other environments in which they are employed. Preferred such monomers are encompassed by the general formula (I):

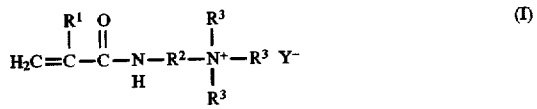

wherein $Y^-$ is fluoride or a fluoride-containing anion, $R^1$ is —H or methyl, $R^2$ is a divalent $C_1$–$C_{12}$ alkylene radical, and each $R^3$, which may be the same as or may differ from one another, is H, a $C_1$–$C_{16}$ alkyl or hydroxyalkyl, or a group of the formula (II), (III) or (IV):

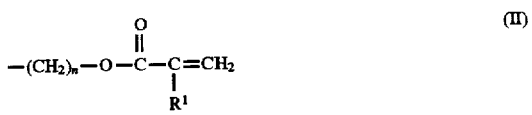

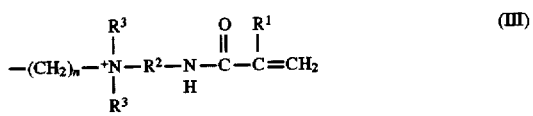

wherein $R^1$, $R^2$ and $R^3$ are as defined above, n is an integer from 1 to 12, preferably 2 to 6, and each $R^4$, which may be the same as or may differ from one another, is H; lower alkyl or lower hydroxyalkyl (including mono- and polyhydroxyalkyl) such as hydroxymethyl, 1,2-dihydroxyethyl, hydroxypropyl, for example 2,3-dihydroxypropyl (e.g. —CH$_2$CHOHCH$_2$OH) or 1,3-dihydroxypropyl (e.g. —CH(CH$_2$OH)$_2$), hydroxybutyl, for example tris(hydroxymethyl)methyl (i.e. —C(CH$_2$OH)$_3$); or an amide group of the formula —CH(CH$_2$OH)(CONHCH$_2$CH$_2$OH).

Another preferred embodiment of the invention provides a polymerizable monomer, preferably an acrylic or methacrylic acid-based monomer, bearing an anion exchange site carrying a protonated, fluoride-containing anion of the formula $[(HF)_xF]^-$ wherein x is an integer from 1 to about 7. Monomers carrying such protonated, fluoride-containing anions exhibit superior chemical stability as compared to corresponding monomers carrying the simple fluoride ion ($F^-$).

Another preferred embodiment of the present invention provides a dental resin material comprising a reaction product of a monomer of the invention as specified above, with at least one other acrylate or methacrylate monomer, with the proviso that at least one of the reacted monomers is a crosslinking agent (i.e. has at least two polymerizable groups in the molecule). In accordance with one aspect of the invention, the crosslinking agent itself can carry one or more fluoride ions or fluoride-containing anions such as those of the formula $[(HF)_xF]^-$ wherein x is as defined above.

Another preferred embodiment provides a fluoride ion-releasing polymerizable monomer, preferably an acrylic or methacrylic acid-based monomer, bearing a chelation site carrying fluoride or a fluoride-containing anion. In such monomers, the chelation of the fluoride or fluoride-containing anion, for example promoted by hydrogen bonding, will enable resins formed from the monomers to release fluoride ions over time.

Another preferred embodiment of the invention provides a method for preparing a dental resin material which comprises the step of copolymerizing a monomer of the invention as specified above with at least one other acrylic acid or methacrylic acid-based monomer, with the proviso that at least one of the reacted monomers is a crosslinking agent.

Still another preferred embodiment of the invention provides a method for preparing an acrylamide or methacrylamide monomer of formula (I). The method comprises reacting a compound of the formula:

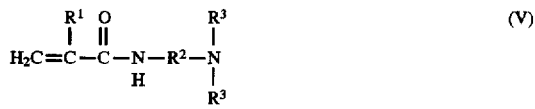

with a compound of the formula $R^3—X$, wherein $R^1$, $R^2$ and $R^3$ are as defined above and X is a leaving group such as Cl, Br, I or an alkylsulfonate or arylsulfonate (i.e. $SO_3R$ wherein R is alkyl or aryl), to thereby form a compound of the formula:

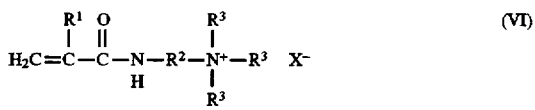

and exchanging $X^-$ for fluoride or a fluoride-containing anion, so as to prepare a fluoride-releasing monomer of formula (I). In a preferred mode, the exchange is achieved by contacting the monomer (VI) with an anion-exchange resin loaded with a fluoride or fluoride-containing anion.

The invention provides novel fluoride ion-releasing monomers that may be effectively polymerized along with other monomers to prepare fluoride ion-releasing dental resin materials. The novel fluoride ion-releasing monomers can be prepared from relatively inexpensive and readily available starting materials in good yield. Advantageously, dental resin materials prepared using the inventive monomers have excellent sustained levels of release of fluoride ion and demonstrate acceptable hardness, durability and other physical and chemical characteristics.

Additional embodiments, features and advantages of the invention will be apparent from the description which follows.

DESCRIPTION OF THE PREFERRED EMBODIMENT

For the purposes of promoting an understanding of the principles of the invention, reference will now be made to certain embodiments thereof and specific language will be used to describe the same. It will nevertheless be understood that no limitation of the scope of the invention is thereby intended, such alterations and further modifications of the principles of the invention as described herein being contemplated as would normally occur to one skilled in the art to which the invention relates.

The invention provides acrylic- or methacrylic acid-based dental resin compositions which deliver fluoride when bonded in place on dental surfaces without degradation of the resin composition. Acrylic- or methacrylic acid-based dental resin compositions are well known and widely used. The compositions of the invention are acrylic- or methacrylic-based compositions, which are the reaction products of a number of components. A first component is a conventional acrylic or methacrylic acid-based monomer, typically an acrylic or methacrylic acid ester. Conventionally, the alkyl radical of the acrylic or methacrylic ester contains about 1 to 12 carbon atoms ("a $C_1$ to $C_{12}$ alkyl group"), and even more conventionally is a $C_1$ to $C_5$ alkyl group. Other ester groups can be used, to the extent that they do not detrimentally interfere with the particular properties desired of the final resin.

Representative known acrylates and methacrylates which may be utilized thus include those in which the alkyl radical of the ester group is methyl, ethyl, isopropyl, butyl, capryl, palmityl, stearyl, lauryl, bis-glycidyl, 2-hydroxyethyl, 1,3-butylene glycol, and the like. Other derivatives of acrylic and methacrylic acid which are suitable for use in the invention include various bisphenol A derivatives of acrylic and methacrylic acid such as those noted in the above-cited patents to Rawls et al., such as 2,2-Bis[4-methacryloyloxyphenyl]propane; 2,2-Bis[4-(2-methacryloyloxy-ethoxy)phenyl]propane; 2,2-Bis[4-(3-methacryloyloxy-propoxyphenyl]propane; the dimethacrylate derivative of 1,2-cyclohexanedicarboxylic acid; the dimethacrylate derivative of 4-cyclohexene-1,2-dicarboxylic acid; and dimethacrylate monomers containing urethane groups such as UEDMA and TUDMA.

The reaction product will generally include a crosslinking monomer which has at least two polymerizable groups per molecule. The crosslinker may be conventional or may be a crosslinking monomer of the invention as described herein. Representative conventional crosslinking monomers that may be used in the invention include, for example, dimethacrylate monomers such as ethylene glycol dimethacrylate, trimethyleneglycol dimethacrylate, and polyethyleneglycol dimethacrylate.

The reaction product of the invention also includes a novel fluoride-releasing monomer of the invention. In one preferred embodiment an inventive acrylamide or methacrylamide monomer may be used which is encompassed by the formula (I):

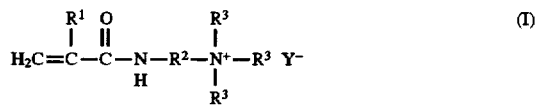

wherein $Y^-$ is a fluoride or fluoride-containing anion, $R^1$ is —H or methyl, $R^2$ is a divalent $C_1$-$C_{12}$ alkylene radical, suitably a lower alkylene radical (i.e. $C_1$ to about $C_6$), and each $R^3$, which may be the same as or may differ from one another, is H, $C_1$-$C_{16}$ alkyl or hydroxyalkyl (including mono- and polyhydroxyalkyl), or a group of the formula (II), (III) or (IV):

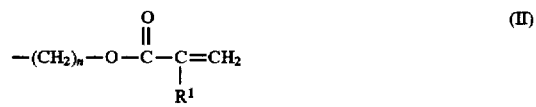

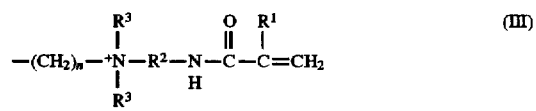

wherein $R^1$, $R^2$ and $R^3$ are as defined above and each $R^4$, which may be the same as or may differ from one another, is H; lower alkyl (i.e. $C_1$ to $C_6$) or lower hydroxyalkyl (including mono- and polyhydroxyalkyl) such as hydroxymethyl, 1,2-dihydroxyethyl, hydroxypropyl, for example 2,3-dihydroxypropyl (e.g. —$CH_2CHOHCH_2OH$) or 1,3-dihydroxypropyl (e.g. —CH ($CH_2OH)_2$), hydroxybutyl, for example tris(hydroxymethyl)methyl (i.e. —C(CH$_2$OH)$_3$); or a group of the formula —CH(CH$_2$OH)(CONHCH$_2$CH$_2$OH). Advantageously, where at least one group R$^4$ contains two or more hydroxyl or amino functions, or a combination thereof, the inventive monomer can contain a chelating moiety for chelating fluoride ions, as opposed to or in addition to an ion-exchange site. Thus, another broad aspect of the invention provides a polymerizable monomer such as an acrylic acid or methacrylic acid-based monomer bearing a chelation site carrying a fluoride or fluoride-containing anion. As indicated above, the chelation site will typically be provided by an organic moiety (e.g. having up to about 20 carbon atoms, preferably up to about 10 carbon atoms) containing two or more nitrogen (N) or oxygen (O) containing groups, for example hydroxyl and/or amino functions, which is effective to chelate a fluoride or fluoride-containing anion.

In accordance with one aspect of the invention, one or more monomers of formula (I) will be included in the overall reaction mixture in order to provide a caries-inhibiting amount of fluoride release from the resin. Preferred are monomers (I) wherein R$^2$ is —(CH$_2$)$_m$ wherein m is 2 to 6, and/or wherein two of the groups R$^3$ are lower alkyl such as methyl or ethyl. Advantageously, where at least one group R$^3$ is of formula (II) or (III), the inventive monomer can serve as a crosslinking agent. Another preference exists when two groups R$^3$ are lower alkyl groups such as methyl or ethyl and the third group R$^3$ is methyl, ethyl, or a polar group such as a hydroxyalkyl or amido group of formula (IV). These lower alkyl and polar groups have been found to provide monomers which form harder resins which effectively release fluoride over an extended period of months.

Inventive fluoride-releasing monomers can be prepared by a series of steps including reacting a compound of the formula:

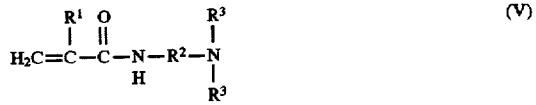

with a compound of the formula R$^3$—X, wherein R$^1$, R$^2$ and R$^3$ are as defined above, and wherein X is a leaving group such as —Cl, —Br, —I or —SO$_3$R wherein R is alkyl such as C$_1$ to C$_{16}$ alkyl, aryl such as phenyl or lower-alkyl-substituted phenyl (e.g. toluenesulfonate such as p-toluenesulfonate), or combined alkyl-aryl, to form a compound of the formula:

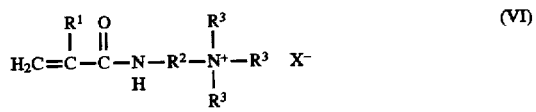

and exchanging X$^-$ for a fluoride ion or a fluoride-containing anion. This exchange is preferably accomplished by contacting (VI) with an anion-exchange resin loaded with the desired fluoride or fluoride-containing anion. For example, the anion-exchange resin can be a polymer containing aliphatic quaternary ammonium functions, such as appropriate Amberlite™ resins (e.g. IRA-400) commercially available from Rohm & Haas, or a polymer containing pyridine functions, for example a Reillex™ crosslinked poly(vinylpyridine) resin available from Reilly Industries, Inc. of Indianapolis, Ind., including Reillex™ 425 resin which is a poly(4-vinylpyridine) resin crosslinked with 25% divinylbenzene.

The ion-exchange resin can be loaded with fluoride, for example, by contacting the resin with an aqueous solution of sodium fluoride. The ion-exchange resin can be loaded with a fluoride-containing polyatomic anion, in particular a protonated fluoride ion of the formula [(HF)$_x$F]$^-$ wherein x is an integer from 1 to about 7, by contacting the resin with liquid hydrogen fluoride or a solution of hydrogen fluoride in an aqueous solvent, more preferably an alcohol/water solvent. Preferred alcohols for these purposes include lower alcohols (i.e. those having 1 to about 6 carbon atoms) and especially methanol and ethanol. The value for x in the above-defined protonated fluoride-containing anion increases with increasing hydrogen fluoride concentration and/or increasing contact time of the hydrogen fluoride solution with the resin. Thus, the value for x can be controlled as desired by increasing or decreasing the hydrogen fluoride concentration of the solution and/or its contact time with the resin to be loaded. Similarly, after loading, rinsing with an aqueous solution, for example water or a water/alcohol rinse, or with an alcoholic solution, will decrease the value for x. In preferred work to date, the value for x has been 2 or 3.

The loaded ion exchange resin can be contacted with the ion-exchangeable, potential fluoride-bearing monomer, for example of formula (VI), by suspending the resin in solution with the monomer and/or by passing a solution of the monomer, for example in an alcohol, through a resin column containing the loaded resin. In either case the contact leads to an ion exchange whereby the monomer eluting from the resin column carries the fluoride or fluoride-containing anion (Y$^-$) and the original counterion (X$^-$) of the monomer remains on the resin.

The applicants' discovery of the improved chemical stability of resins and resin precursors provided by the anion [(HF)$_x$F]$^-$ also provides means for improving fluoride-bearing polymerizable monomers generally, for example including the ester-based monomers described in the above-cited Rawls et al. patents. This aspect of the invention thus broadly provides an acrylate or methacrylate monomer bearing an ion-exchange site carrying a protonated fluoride anion of the formula [(HF)$_x$F]$^-$ wherein x is an integer from 1 to about 7, more typically from 1 to about 5 and preferably from 2 to 3. As indicated, monomers carrying this anion have exhibited superior stability relative to corresponding monomers which carry the fluoride ion, while nevertheless demonstrating the capacity to successfully form resin materials which release fluoride ion over time.

To form a resin for use as a dental resin material, the above-described components, optionally in the presence of other components which may be conventional, are reacted in the presence of a free radical initiator. The resulting dental resin material releases fluoride ion slowly while not itself undergoing significant degradation.

In one mode of use, one or more components are first combined with an initiator while one or more other components, or additional amounts of the same components, are combined with an accelerator. When, thereafter, the initiator-containing mix is blended with the accelerator-containing mix the polymerization occurs and the dental resin is formed. In this regard, suitable initiators and accelerators which can be used in acrylic- or methacrylic-based polymerizations are well known. Suitable initiators include, for instance, peroxides such as benzoyl peroxide, cumene hydroperoxide, and the like. Representative suitable accelerators include N,N-dimethyl-p-toluidine, dihydroxy ethyl-p-toluidine, 1-acetyl-thiourea, and the like. However, as indicated, suitable initiators and accelerators are in general well known and their use in the invention is well within the purview of the ordinarily skilled artisan.

Of course, additional ingredients are conventionally employed in acrylic- or methacrylic-based dental resin compositions and may be employed in the present invention as well. These include for instance fillers such as inorganic silicates, amorphous silica, glass, quartz, alumina, apatite phosphates and the like, polymerization inhibitors such as hydroquinones, e.g. butylated hydroxy toluidine, butylated hydroxy anisole and methyl ether of hydroquinone.

The following Examples are offered by way of illustration and not by way of limitation. In the Examples, all percentages are percentages by weight unless otherwise indicated.

EXAMPLE 1

Dodecyl Monomer 3-(Methacryloylamino)propyldimethylamine (8.9 g, 0.05 mol) and dodecyl bromide (14.9 g, 0.06 mol) were dissolved in 50 ml of $CH_3CN$. The mixture was stirred at room temperature. After 48 hours the solvent was evaporated under vacuum. The solid residue contained about 100% alkylated methacrylic monomer with bromide anion (by $^1$H-NMR analysis). Fluoride ion exchange was performed by passing a methanol solution of the bromide salt through a column packed with the loaded form of Reillex 425 polymer (commercially available from Reilly Industries, Inc., Indianapolis, Ind.), which was loaded with the fluoride anion $[(HF)_xF]^-$ wherein x=2 by the following procedure. Reillex 425 resin was treated with portions of 1N aqueous NaOH solution until no bromide or chloride ion could be detected with acidic $AgNO_3$ solution. Next, the column was washed with de-ionized water until neutral to pH paper, collected on a Buchner funnel and washed with three resin volumes of methanol. The resin was transferred to a standard chromatography column and treated with 0.5–1.0N HF solution (prepared by dilution of commercial 48–50% hydrofluoric acid with methanol) until the pH of the effluent was 3–4. The resin bed was finally rinsed with one column volume of methanol before use. The 3-(methacryloylamino)-propyldimethyldodecylammonium polyhydrogen fluoride-fluoride was purified by recrystallization from acetone. The fluoride product is a white solid, m.p.=113°–118° C. The monomers were characterized by $^1$H-NMR (multiplicity, J. (Hz), area, assignment) (Solvent: $CD_3OD$) $^1$H: δ0.79 (t, 6, 3, $CH_3$), 1.19 (br, s, 15, 16, $CH_2$), 1.26 (m, 10, 2, $CH_2$), 1.62 (m, 15, 2, $CH_2$), 1.84 (s, 3, $CH_3$), 1.87 (m, 2, $CH_2$), 2.97 (s, 6, $CH_3$), 3.2 (m, 4, $CH_2$), 5.29 (s, 1, C=CH), 5.68 (s, 1, =CH); IR, (cm$^{-1}$, intensity, assignment); (728, s, br,), (933, s, C=$CH_2$), (1474, m, $CH_2$—N), (1614, s, C=C), (1663, s, amide), (2927, s, $CH_2$ in alkyl chain) and elemental analysis: Found (%): C, 60.36, H 10.91, N 6.72, F 13.82, Br undetectable.

EXAMPLE 2

Ethyl Monomer

The preparative procedure of Example 1 was repeated, except replacing dodecyl bromide with ethyl bromide. The resulting product, 3-(methacryloylamino)propyldimethylethylammonium polyhydrogen fluoride-fluoride monomer, was a crystalline solid having a melting point of 73°–78° C.). $^1$H-NMR analysis yielded the following results: (Solvent: $CD_3OD$) $^1$H: δ6.1, 5.7 (s, 2H, $CH_2$=), 3.7 (m, 6H, $NCH_2$), 3.4 (s, 6H, $N(CH_3)_2$), 2.3 (m, 2H, $CH_2$, 2.2 (s, 3H, $CH_3$), 1.6 (t, a3H, $CH_3$). Similarly, $^{13}$C NMR: δ8.3, 18.3, 23.7, 37.6, 50.7, 60.6, 62.5, 121.0, 140.9, 171.4.

EXAMPLE 3

Butyl Monomer

The preparative procedure of Example 1 was repeated, except replacing dodecyl bromide with butyl bromide. The resulting product, 3-(methacryloylamino)propyldimethylbutylammonium polyhydrogen fluoride-fluoride monomer, was a crystalline solid having a melting point of 92°–96° C. $^1$H-NMR analysis yielded the following results: (Solvent: $CD_3OD$) $^1$H: δ5.8, 5.4 (s, 2H, $CH_2$=), 3.4 (m, 6H, $NCH_2$), 3.1 (s, 6H, $N(CH_3)_2$), 2.0 (m, 2H, —$CH_2$—), 1.95 (s, 3H, —$CH_3$), 1.7 (m, 2H, $NCH_2$—$CH_2$—), 1.4 (t, 2H, $NCH_2CH_2$—$CH_2$—), 1.0 (t, 3H, $CH_3$), $^{13}$C: δ13.9, 18.8, 20.6, 23.8, 25.4, 37.6, 51.4, 62.9, 65.0, 121.1, 140.9, 171.4. Elemental analysis: Found (%)C, 53.85, H, 9.65, N, 9.74, F, 17.88, Br, undetectable. Analytical data suggests that fluoride is in the form of the $H_2F_3^-$ anion.

EXAMPLE 4

Hexyl Monomer

The preparative procedure of Example 1 was repeated, except replacing dodecyl bromide with hexyl bromide. The product, 3-(methacryloylamino)propyldimethylhexylammonium polyhydrogen fluoride-fluoride monomer, was a crystalline solid having a melting point of 115°–120° C. $^1$H-NMR analysis yielded the following results: (Solvent: $CD_3OD$) $^1$H: δ5.8, 5.4 (s, 2H, $CH_2$=), 3.4 (m, 6H, $NCH_2$), 3.1 (s, 6H, $N(CH_3)_2$), 2.0 (m, 2H, —$CH_2$—), 1.95 (s, 3H, —$CH_3$), 1.7 (broad s, 2H; $NCH_2$—$CH_2$), 1.4 (s, 6H, —$(CH_2)_3$), 1.9 (t, 3H, $CH_3$), $^{13}$C: δ–0.02, 14.2, 18.7, 23.5, 23.8, 27.1, 32.5, 37.4, 37.6, 51.4, 62.8, 65.2, 121.1, 140.9, 171.4. Elemental analysis: Found C, 54.94, H, 9.85, N, 8.68, F, 17.51, Br, undetectable. Analytical data suggests that fluoride is in the form of the $H_2F_3^-$ anion.

EXAMPLE 5

Octyl Monomer

The preparative procedure of Example 1 was repeated, except replacing dodecyl bromide with octyl bromide. The resulting product, 3- (methacryloylamino) propyldimethyloctylammonium polyhydrogen fluoride-fluoride monomer, was a crystalline solid having a melting point of 118°–121° C. $^1$H-NMR analysis yielded the following results: (Solvent: $CD_3OD$) $^1$H: δ5.8, 5.4 (s, 2H, $CH_2$=), 3.4 (m, 6H, $NCH_2$—), 3.1 (s, 6H, $N(CH_3)_2$), 2.0 (m, 2H, —$CH_2$—), 1.95 (s, 3H, $CH_3$), 1.7 (broad s, 2H, $NCH_2$—$CH_2$—), 1.4 (d, 10H, —$(CH_2)_3$—)$_2$), 0.9 (t, 3H, $CH_3$), $^{13}$C: δ0.05, 14.4, 14.5, 18.8, 23.6, 23.8, 27.4, 30.3, 32.9, 37.6, 51.4, 62.9, 65.2, 121.1, 140.9, 171.4.

EXAMPLE 6

Decyl Monomer

The preparative procedure of Example 1 was repeated, except replacing dodecyl bromide with decyl bromide. The product, 3-(methacryloylamino) propyldimethyldecylammonium polyhydrogen fluoride-fluoride, was a crystalline solid having a melting point of 122°–126° C. $^1$H-NMR analysis yielded the following results: (Solvent: $CD_3OD$) $^1$H: δ5.8, 5.4 (s, 2H, $CH_2$=), 3.4 (m, 6H, $NCH_2$—), 3.1 (s, 6H, $N(CH_3)_2$) 3.4 (m, 6H, $NCH_2$—), 3.1 (s, 6H, $N(CH_3)_2$), 2.0 (m, 2H, —$CH_2$—), 1.95 (2, 3H, $CH_3$), $^{13}$C: δ0.03, 14.7, 14.8, 19.1, 23.8, 24.1, 27.7, 30.6, 30.7, 30.9, 33.1, 37.8, 51.7, 63.2, 65.5, 121.4, 141.2, 171.6.

EXAMPLE 7

Acetamido Monomer

The preparative procedure of Example 1 was repeated, except replacing dodecyl bromide with 2-bromoacetamide.

The product, 3-(methacryloylamino) propyldimethylacetamidoammonium polyhydrogen fluoride-fluoride monomer, was a crystalline solid having a melting point of 250° C.:(d). $^1$H-NMR analysis yielded the following results: (Solvent: CD$_3$OD) $^1$H: δ5.8, 5.4 (s, 2H, CH$_2$=), 4.2, 3.6, 3.4 (s, m, m, 6H, NCH$_2$—), 3.3 (s, 6H, N(CH$_3$)$_2$), 2.1 (m, 2H, —CH$_2$—), 1.9 (s, 3H, CH$_3$), $^{13}$C: δ18.8, 23.9, 27.5, 52.3, 62.8, 64.4, 120.9, 140.9, 167.6, 171.3. Elemental analysis: Found C, 42.84, H, 7.39, N, 13.54, F, 20.67, Br, undetectable. Analytical data suggests that fluoride is in the form of the H$_2$F$_3$— anion.

EXAMPLE 8

Hydroxyethyl Monomer

The preparative procedure of Example 1 was repeated, except replacing dodecyl bromide with hydroxyethyl bromide. The resulting product, 3-(methacryloylamino) propyldimethyl-hydroxyethylammonium polyhydrogen fluoride-fluoride, was a non-crystalline waxy solid. $^1$H-NMR analysis yielded the following results: (Solvent: CD$_3$OD) $^1$H: δ5.8, 5.4 (s, 2H, CH$_2$=), 4.0, 3.4, 3.35 (m, 6H, NCH$_2$—), 3.2 (s, 6H, N(CH$_3$)$_2$), 2.1 (m, 2H, —CH$_2$—), 1.95 (s, 3H, CH$_3$), $^{13}$C: δ18.8, 23.9, 37.6, 52.3, 47.0, 64.4, 66.5, 121.0, 141.0, 171.4.

EXAMPLE 9

Tetramethylene Difluoride Cross-linker

A tetramethylene difluoride cross-linker, specifically 1,4-bis-[3-(methacryloylamino)propyldimethylammonium] butane difluoride, was prepared as follows. A mixture of 3-(methacryloylamino)propyldimethylamine (9.37 g, 0.055 mol) and 1,4-dibromobutane (5.40 g, 0.025 mol) in acetonitrile (50 ml) was stirred at room temperature for 48 hours. The bis-quaternary ammonium dibromide was collected by filtration after crystalization from acetonitrile in 94.5% yield, mp 149.5°–150° C.

Fluoride ion-exchange was performed by two methods:

1) The dibromide salt was treated with an equivalent amount of AgF in methanol at room temperature. The difluoride product was obtained after filtration to remove AgBr and evaporation under reduced pressure of the filtrate. Further purification was achieved by recrystallization from acetonitrile.

2) A methanol solution of the dibromide salt was passed through a column packed with the F$^-$ form of Amerlite IRA-400 ion-exchange resin. The difluoride product was obtained by the procedure described in Example 1. The ion-exchange resin was loaded with fluoride ion by the following procedure. The commercial IRA-400 (Cl$^-$ form) resin was first converted to its OH$^-$ form by washing with a 5% aqueous NaOH solution until no chloride ion could be detected in the effluent with acidic AgNO$_3$ solution, followed by rinsing the resin bed with water until neutral to pH paper. Then, the OH$^-$ form of IRA-400 resin was converted to fluoride form by passing a 4% aqueous NaF solution until the pH value of the effluent was the same as that of NaF solution (~7.5), followed by rinsing the resin bed with water until neutral to pH paper. The IRA-400 (F$^-$) resin suspension in water was filtered and washed with methanol.

The resulting difluoride cross-linker is a crystalline solid with a melting point of 160° C. (d). $^1$H-NMR analysis yielded the following results. (Solvent, D$_2$O) $^1$H: δ5.75, 5.42 (S, 4H, CH$_2$=), 3.30–3.45 (m, 12H, —NCH$_2$—), 3.11 (S, 12H, —N(CH$_3$)$_2$), 2.00–2.15 (m, 4H —CH$_2$—), 1.95 (S, 6H, —C=C(CH$_3$)—), 1.80–1.90 (m, 4H, —CH$_2$—). Elemental analysis, Found (%), C, 56.04, H, 10, 15, N, 11.87, F, 7.85. Analytical data suggests that fluoride is in the form of the F$^-$ anion.

EXAMPLES 10–11

The preparative procedure of Example 9 was repeated, except replacing 1,4-dibromobutane with bromoethane or bromoacetamide. Analytical data suggests that the resulting fluorides, 3-(methacryloylamino) propylethyldimethylammonium fluoride and 3-(methacryloylamino) propyldimethylacetamidoammonium fluoride, are in the form of the F$^-$ anion.

EXAMPLE 12

Methyl Fluoride Monomer 3-(Methacryloylamino)propyltrimethylammonium chloride (Aldrich) was ion-exchanged with IRA-400 (F) in water or in methanol using the procedures of Example 9. The resulting fluoride salt is a crystalline solid having a melting point of 110°–113° C. (d). $^1$H-NMR analysis yields the following results (solvent D$_2$O) $^1$H: δ5.70, 5.46 (S, 2H, CH$_2$=), 3.33–3.36 (m, 4H, —N CH$_2$—) 3.11 (S, 9H, —N(CH$_3$)$_3$), 2.05~2.06 (m, 2H, —CH$_2$—), 1.92 (S, 3H, C=C—CH$_3$). Elemental analysis, Found (%): C, 53.43, H, 10.15, N, 12.38, F, 8.25. Analytical data suggest that the fluoride is in the form of the F$^-$ anion.

EXAMPLE 13

Resin Formulation with Dodecyl Monomer

A resin for testing fluoride release was prepared according to the formulation given in Table 1.

TABLE 1

| Component | Part A | Part B |
| --- | --- | --- |
| Methacrylic Acid | 0.75 ml | 0.75 ml |
| Trimethylpropanetrimethacrylate | 0.75 ml | 0.75 ml |
| Ethyleneglycol dimethacrylate | 2.15 ml | 2.15 ml |
| Fluoride Monomer of Ex. 1 | 130 mg | 130 mg |
| Benzoyl peroxide | 20 mg | — |
| N,N-Dimethyl p-toluidine | — | 10 mg |
| MEHQ | 200 ppm | 200 ppm |

After mixing together parts A and B in a disk die, an exothermic curing occurred. The specimens of resin in the form of disk samples (10 mm diameter×3 mm thick) were evaluated for average daily fluoride ion release over a thirty day period (μg/cm$^2$/day) alongside commercially available materials, by suspending the disks in deionized water and measuring the accumulation of fluoride ion over time using an ion-specific electrode. The results are set forth in Table 2.

TABLE 2

| Material | Release |
| --- | --- |
| Inventive Resin | 6.5 |
| Fluoroever | 1.4 |
| Fluorocore | 1.5 |
| FluoroShield | 0.4 |
| AllBond Linear-F | 0.2 |

EXAMPLES 14–15

Resin Formulation with Ethyl Monomer

Resin disks were prepared as in Example 13, except incorporating the ethyl monomer of Example 2 according to the formulation given in Table 3.

TABLE 3

| Component | Part A | Part B |
| --- | --- | --- |
| Methacrylic Acid | 0.25 ml | 0.25 ml |
| Trimethylpropanetrimethacrylate | 0.25 ml | 0.25 ml |
| Ethyleneglycol dimethacrylate | 0.75 ml | 0.75 ml |
| Fluoride Monomer B | * | — |
| Benzoyl peroxide | 20 mg | — |
| N,N-Dimethyl-p-toluidine | — | 10 mg |

*Two samples were prepared, one with 183 mg (4.9% W/W, Example 11) and one with 345 mg (9.0% W/W, Example 12).

The hardness of the resins was tested with a Knoop Hardness apparatus. The resin of Example 11 exhibited a Knoop hardness of 22, while that of Example 12 exhibited a Knoop hardness of 16. Importantly, the fluoride release data indicate that the resins sustain fluoride release at a level (~10 µg/cm²/day) approximately equivalent to that of Fuji II, a fluoride-containing ionomer. The resins also demonstrated significantly improved hardness compared to the resin prepared with the dodecyl monomer of Example 13.

EXAMPLES 16–29

Resin Formulations

Additional resins were prepared using the general procedures and each of the fluoride containing monomers ("F-Monomers") described in the Examples above, loaded to 5% to 7.5% in each of Parts A and B, as summarized in Tables 4 and 5.

TABLE 4

| Component | Part A | Part B |
| --- | --- | --- |
| bis-phenol-A-Glycidyl methacrylate | 23.1% | 23.1% |
| triethylene glycol dimethacrylate | 33.4% | 33.4% |
| methacrylic acid | 3.15% | 3.15% |
| benzoyl peroxide | 0.25% | — |
| N,N-dimethyl-p-toluidine | — | 0.11% |
| F-Monomer | 5%–7.5%–27% | 5%–7.5%–27% |
| Microfiller* (coupling agent**) | 27% | 27% |
| Microfiller* | 7.5%–5% | 7.5%–5% |

*Degussa AEROSIL 130 microfiller
**Denotes microfiller treated with 3-methacryloyloxypropyl-trimethoxy silane

TABLE 5

| Example | Monomer of | Part A | Part B |
| --- | --- | --- | --- |
| 16 | Example 2 | 5% | 5% |
| 17 | Example 3 | 7.5% | 7.5% |
| 18 | Example 4 | 7.5% | 7.5% |
| 19 | Example 5 | 7.5% | 7.5% |
| 20 | Example 6 | 7.5% | 7.5% |
| 21 | Example 1 | 5% | 5% |
| 22 | Example 1 | 7.5% | 7.5% |
| 23 | Example 7 | 7.5% | 7.5% |
| 24 | Example 9 | 7.0% | 7.0% |
| 25 | Example 10 | 7.0% | 7.0% |
| 26 | Example 12 | 7.0% | 7.0% |

In addition, the monomer of Example 1 was used to prepare similar formulations loaded to 10% (Example 27) and 20% (Example 28) in Parts A and B by increasing the amount of monomer used. Similarly, the monomer of Example 7 was used to prepare an additional formulation loaded to 10% (Example 29). In each case, resins were formed which release fluoride over time.

EXAMPLES 30–31

Evaluation of Adhesive Properties

The resins of Examples 18 and 19 were evaluated for tensile bond strength compared to Phase IIT (Reliance Orthodontic Products, Itasca, Ill.), a commercially available, fluoride-free two paste chemical cure resin adhesive used for orthodontic bonding. Tensile bond strength testing utilized commercially available stainless steel brackets from Ormco Orthodontics (Glendora, Calif.). The brackets were designed for maxillary central incisors, had no torque or angulation, and had mesh backed bases. The brackets were bonded to 51 bovine incisors using the resins of Examples 18 and 19. The teeth were first examined visually and determined to be free of gross irregularities, enamel cracks, or debris. They were then prepared for bonding by first removing the roots at the cemento-enamel junction and extraneous mesial, distal, and incisal areas. Only the middle third of the labial surface was utilized for bonding. The facial surfaces were flattened by grinding with coarse and fine grit sicpaper under running water, and each tooth was embedded in a self-curing epoxy resin. Comparison of the inventive and control resins by ANOVA followed by General Linear Models multiple comparisons revealed that the resins of Examples 18 and 19 had bond strengths of 4.45±0.65 MPA and 3.83±0.76 MPa, respectively, and the control had a bond strength of 5.31±0.97 MPa.

While the invention has been described above in some detail, it will be understood that certain modifications and variations can be made without departing from the spirit and scope thereof.

What is claimed is:

1. A dental resin material comprising a solid reaction product of a monomer of the formula:

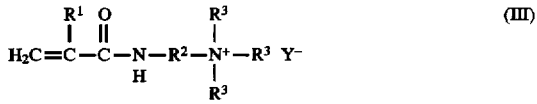

(III)

$$H_2C=\overset{R^1}{\underset{|}{C}}-\overset{O}{\overset{||}{C}}-\underset{H}{N}-R^2-\overset{R^3}{\underset{|}{N^+}}-R^3 \; Y^-$$

wherein Y⁻ is a fluoride or fluoride-containing anion, $R^1$ is —H or methyl, $R^2$ is a divalent $C_1$–$C_{12}$ alkylene radical, and each $R^3$, which may be the same as or may differ from one another, is H, $C_1$–$C_{16}$ alkyl or hydroxyalkyl, or a group of the formula

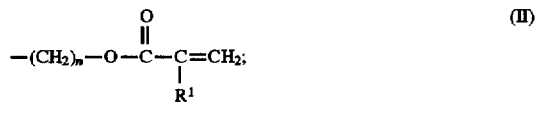

(II)

$$-(CH_2)_n-O-\overset{O}{\overset{||}{C}}-\underset{\underset{R^1}{|}}{C}=CH_2;$$

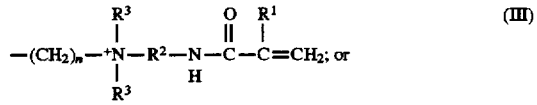

(III)

$$-(CH_2)_n-\overset{R^3}{\underset{\underset{R^3}{|}}{{}^+N}}-R^2-\underset{H}{N}-\overset{O}{\overset{||}{C}}-\overset{R^1}{\underset{|}{C}}=CH_2; \text{ or}$$

(IV)

$$-(CH_2)_n-\overset{O}{\overset{||}{C}}-N(R^4)_2;$$

wherein $R^1$, $R^2$ and $R^3$ are as defined above, n is an integer from 1 to about 12, and each $R^4$, which may be the same as or may differ from one another, is H, lower alkyl, lower hydroxyalkyl, or an amide group of the formula —CH($CH_2OH$)($CONHCH_2CH_2OH$);

with at least one other polymerizable acrylic or methacrylic monomer, with the proviso that at least one of the reacted monomers is a free radical polymerizable crosslinking agent.

2. The dental resin material of claim 1 wherein $Y^-$ is $((HF)_xF)^-$ wherein x=1 to 7.

3. The dental resin material of claim 2 wherein $R^1$ is —$CH_3$, $R^2$ is —$(CH_2)_3$—, and each $R^3$ is lower alkyl, lower hydroxy alkyl, or an amide group of formula (IV) as defined in claim 1 wherein each group $R^4$ is H.

4. The dental resin material of claim 3 wherein two groups $R^3$ are methyl and the third group $R^3$ is ethyl or 2-hydroxyethyl.

5. A dental resin material comprising a reaction product of a first monomer which is a fluoride ion-releasing polymerizable monomer bearing an anion exchange site carrying a fluoride-containing anion of the formula $((HF)_xF)^-$ wherein x is an integer from 1 to 7, with at least one other monomer which is an acrylic or methacrylic monomer, with the proviso that at least on of said monomers is a crosslinking monomer.

6. The dental resin material of claim 5 wherein x is 2 or 3.

7. The dental resin material of claim 5 wherein said first monomer is an acrylic acid or methacrylic acid monomer.

8. The dental resin material of claim 7 wherein said first monomer is an acrylate, methacrylate, acrylamide or methacrylamide monomer.

9. The dental resin material of claim 8 wherein x is 2 or 3.

10. The dental resin material of claim 2, wherein at least one group $R^3$ is a group of the formula II.

11. The dental resin material of claim 2 wherein at least one group $R^3$ is a group of the formula III.

12. The dental resin material of claim 2 wherein at least one group $R^3$ is a group of the formula IV.

13. The dental resin material of claim 1, which comprises a reaction product of said at least one other polymerizable acrylic or methacrylic acid monomer with a monomer selected from the group consisting of:

3-(methacryloylamino)propyldimethylamine polyhydrogen fluoride-fluoride;

3-(methacryloylamino)propyldimethylethylammonium polyhydrogen fluoride-fluoride;

3-(methacryloylamino)propyldimethylhexylammonium polyhydrogen fluoride-fluoride;

3-(methacryloylamino)propyldimethyloctylammonium polyhydrogen fluoride-fluoride;

3-(methacryloylamino)propyldimethyldecylammonium polyhydrogen fluoride-fluoride;

3-(methacryloylamino)propyldimethylhydroxyethylammonium polyhydrogen fluoride-fluoride;

1,4-bis-(3-(methacryloylamino)propyldimethylammonium)butane difluoride;

3-(methacryloylamino)propylethyldimethylammonium fluoride;

3-(methacryloylamino)propyldimethylacetamidoammonium fluoride; and 3-(methacryloylamino)propyltrimethylammonium fluoride.

14. The dental resin material of claim 13 which also comprises an acrylic or methacrylic acid ester.

15. The dental resin material of claim 1, and also including an inorganic filler.

16. The dental resin material of claim 15, which includes a reaction product of said at least one other acrylic or methacrylic acid monomer with 3-(methacryloylamino) propyldimethylethylammonium polyhydrogen fluoride-fluoride.

* * * * *

UNITED STATES PATENT AND TRADEMARK OFFICE
CERTIFICATE OF CORRECTION

PATENT NO.   : 5,705,581
DATED        : January 6, 1998
INVENTOR(S)  : Wilmer K. Fife et al.

It is certified that error appears in the above-indentified patent and that said Letters Patent is hereby corrected as shown below:

In col. 11, line 9, the last line under the "Component" column of Table 3, please delete the "-" between the words "Dimethyl" and "p".

In col. 11, line 40, under the columns labelled "Part A" and "Part B", respectively, please delete "5%-7.5%-27%" in each instance and replace each instance with-- 5% - 7.5%- --.

Signed and Sealed this

Eighteenth Day of May, 1999

Attest:

Q. TODD DICKINSON

Attesting Officer    Acting Commissioner of Patents and Trademarks